United States Patent [19]

Parrish

[11] E Patent Number: Re. 33,686

[45] Reissued Date of Patent: Sep. 10, 1991

[54] URINE SPECIMEN COLLECTORS AND METHOD OF DETECTING SPURIOUS URINE SPECIMENS

[75] Inventor: James M. Parrish, Midlothian, Va.

[73] Assignee: Medical Implements, Inc., Richmond, Va.

[21] Appl. No.: 423,787

[22] Filed: Oct. 18, 1989

Related U.S. Patent Documents

Reissue of:

[64] Patent No.: 4,832,046
Issued: May 23, 1989
Appl. No.: 140,254
Filed: Dec. 31, 1987

U.S. Applications:

[63] Continuation-in-part of Ser. No. 65,933, Jun. 24, 1987, abandoned.

[51] Int. Cl.[5] ..... A61B 5/00

[52] U.S. Cl. ..... 128/771; 128/736; 604/318

[58] Field of Search ..... 128/760, 761, 771, 736; 604/317, 318; 4/110

[56] References Cited

U.S. PATENT DOCUMENTS

| | | | |
|---|---|---|---|
| 3,335,714 | 8/1967 | Giesy | 128/2 |
| 3,518,164 | 6/1970 | Andelin et al. | 195/127 |
| 3,620,889 | 11/1971 | Baltzer | 161/5 |
| 3,625,654 | 12/1971 | Van Duyne | 23/253 |
| 3,661,142 | 5/1972 | Flam | 128/2 H |
| 3,750,647 | 8/1973 | Gleason et al. | 128/2 F |
| 3,811,136 | 5/1974 | Whitney et al. | 4/110 |
| 3,864,976 | 2/1975 | Parker | 73/356 |
| 3,951,133 | 4/1976 | Reese | 128/2 H |
| 4,064,760 | 12/1977 | Benjamin | 73/421 R |
| 4,154,106 | 5/1979 | Inoue et al. | 73/356 |
| 4,408,905 | 10/1983 | Ehrenkranz | 374/157 |
| 4,466,445 | 8/1984 | Abrams | 128/736 |
| 4,473,530 | 9/1984 | Villa-Real | 422/58 |
| 4,564,299 | 1/1986 | Ehrenkranz | 374/157 |
| 4,589,548 | 5/1986 | Fay | 206/363 |
| 4,651,749 | 3/1987 | Sagi | 128/736 |
| 4,681,572 | 7/1989 | Tokarz et al. | 604/329 |
| 4,682,605 | 7/1987 | Hoffman | 128/736 |

OTHER PUBLICATIONS

"Measurement of Urine Temp . . . . Treatment Program", Judson et al., Am. J. Drug Alcohol Abuse, 6/1979.

*Primary Examiner*—Max Hindenburg
*Attorney, Agent, or Firm*—Staas & Halsey

[57] ABSTRACT

Urine specimen containers combined with a temperature sensitive member which is capable of signalling a spurious urine specimen when placed in a sufficiently close heat exchange relationship with a urine specimen. The temperature sensitive member contains portions which change color irreversibly at preselected temperatures when placed in sufficiently close heat exchange relationship with a urine specimen. The temperatures at which the irreversible color changes are made are selected slightly below normal body temperature and slightly in excess of normal body temperature such as from about 90° F. to about 100° F. The urine specimen collector itself includes a bowl-shaped member with an integral handle. The bowl-shaped member is contoured to fit to close proximity to the body of the user. A cover member is pivotally attached to the handle and functions as a splash guard for the user. The cover member also has a raised boss terminating in an open top to permit urination through the cover member. The opening of the raised boss in the cover member is substantially in line with a threaded connection for a collection container which is screwed onto the bottom of the bowl-shaped member. The cover member has a portion thereof spaced from a frontal portion of the bowl-shaped member to provide an overflow from the bowl-shaped member.

7 Claims, 4 Drawing Sheets

URINE SPECIMEN COLLECTORS AND METHOD OF DETECTING SPURIOUS URINE SPECIMENS

Matter enclosed in heavy brackets [ ] appears in the original patent but forms no part of this reissue specification; matter printed in italics indicates the additions made by reissue.

This is a continuation-in-part application of Ser. No. 65,933, filed June 24, 1987, now abandoned.

This invention relates to urine specimen collectors combined with a method of detecting spurious urine specimens and, more particularly, to a collector having an integral splash guard and the use of a temperature sensitive member attached externally of or within the urine container to verify the genuineness of the specimen.

BACKGROUND OF THE INVENTION

Heretofore it has been known to utilize funnel-shaped introductory members for use in combination with collection containers for sanitary specimen collectors. U.S. design Pat. No. 227,413 Sherin, issued June 19, 1973, U.S. Pat. No. 3,711,871 Sherin, issued Jan. 23, 1973; and U.S. Pat. No. 3,811,136 Whitney et al, issued May 21, 1974 are three examples of specimen collectors using funnel-shaped introductory members. All of these devices suffer from a common defect in that urine is easily splashed back onto the person providing the urine specimen. Another shortcoming of these devices is that they do not possess satisfactory overflow means. In addition to adjunctive use of a funnel-shaped introductory member, there is a growing need in drug screening applications to be able to ascertain that the uring specimen obtained is not spurious, fraudulent, non-authentic or non-current.

SUMMARY OF THE INVENTION

In accordance with the present invention, the aforementioned limitations and shortcomings of the known prior art are effectively overcome. In particular, a urine specimen collector is provided which incorporates a bowl-shaped introductory member to a sanitary collection container. The bowl-shaped member has a threaded bottom opening which allows drainage into an attachment of a collection container. A cover member provides a splash guard for the bowl-shaped member and is pivotally secured to a handle means. The cover member has a raised boss which terminates in an open top that permits urination through the cover member. For rapid and efficient filling of the collector container, the latter is secured to the bowl-shaped member at its threaded opening which is substantially in line with the opening in the raised boss of the cover member. The cover member is recessed from a lowered frontal portion of the bowl-shaped member to provide an overflow therefrom.

In addition, a temperature sensitive member is placed either exteriorly of or within the collector container which is capable of signalling a spurious urine specimen by heat transfer through the collector container or by direct contact with the urine specimen itself. This temperature sensitive member contains portions or discrete areas which change color irreversibly at pre-selected temperatures when placed in close heat exchange relationship with a urine specimen. In order to detect urine specimens which are spurious, fraudulent, non-authentic or non-current in point of time, the temperature sensitive member includes at least one portion or discrete area which will indicate a temperature for the specimen which is slightly less than the normal body temperature and at least one other portion or discrete area which will indicate a specimen temperature slightly in excess of the normal body temperature of 98.6° F. For example, in a preferred form of the invention, a series of temperature sensitive letters or discs are attached to a suitable backing member that is adhesively secured exteriorly of the collector container below the level of urine within the container or to the inside bottom of the collector container. Three sets of letters or disks are employed which are present in their manufacture to change color at about 90° F., 95° F., and 100° F. For a normal urine specimen, the letter sets or discs are manufactured by American Thermometer Co., Inc. of Dayton, Ohio or by Tempil, a division of Big Three Industries, Inc., of South Plainfield, New Jersey.

The inherent advantages and improvements of the present invention will become more readily apparent upon reference to the following detailed description of the invention and by reference to the accompanying drawings.

DETAILED DESCRIPTION OF THE INVENTION

Figure 1:
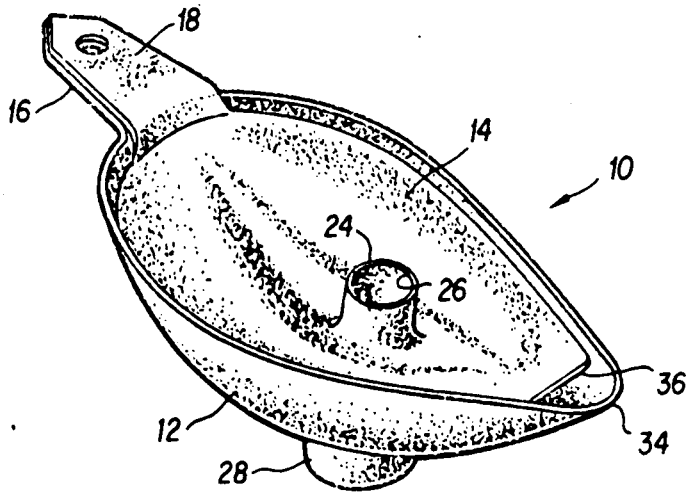
FIG. 1 is a perspective view of a urine specimen collector device made in accordance with the present invention.

Referring now to FIG. 1 of the drawings, there is illustrated a urine specimen introductory collector indicated generally at 10. Included in this urine specimen introductory collector 10 is a bowl-shaped member 12 which is substantially open at its top. A cover member 14 substantially completely closes the open top of the bowl-shaped member 12. Cover member 14 also functions as a splash guard when the urine specimen introductory collector 10 is used in combination with a collection container.

Figure 7:
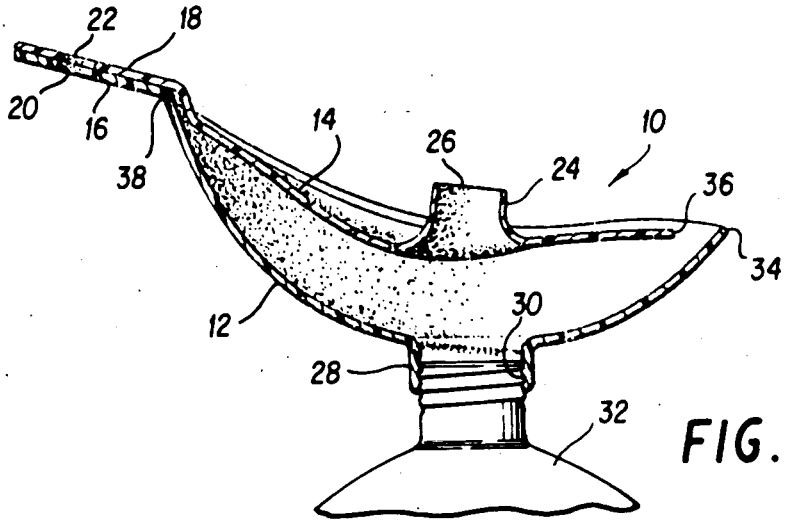
FIG. 7 is an elevational view of the device of FIG. 3 taken in vertical cross section along line 7—7 which a fragmentary illustration of a collection container added thereto.
Figure 2:
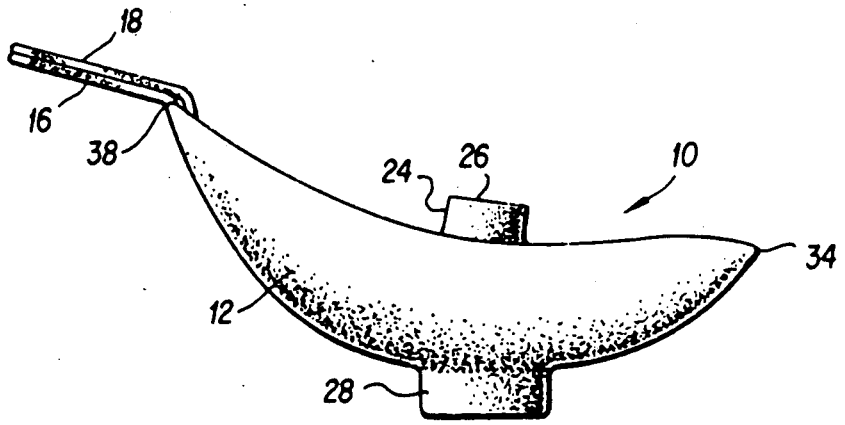
FIG. 2 is a side elevational view of the device of FIG. 1.

The bowl-shaped member 12 is shown to have an integral handle portion 16 at its rearmost and most elevated portion as can be seen in FIGS. 1, 2 and 7. Cover member 14 also has an integral handle portion 18 which overlies the integral handle portion 16 and is secured thereto. In the drawings there is illustrated mating holes or apertures 22 passing through the handle portions 16, 18 through which a fastening member, not shown, may pass. However, in the preferred form of the invention, these two integral handle portions 16 and 18 are heat sealed together providing a pivotal mounting for the cover member 14.

Cover member 14 is further provided with a raised generally cylindrical boss 24 which terminates in a substantially planar open end 26. Substantially directly opposite this opening 26 in the raised cylindrical boss 24 is a tubular outlet stem 28 in the bottom of the bowl-shaped member 12 which is provided with a threaded inner portion 30. A collection container 32 is illustrated in FIG. 7 threadedly secured to the bowl-shaped member 12. For purposes of this invention, the collection container 32 may be of any desired size and shape.

Figure 5:
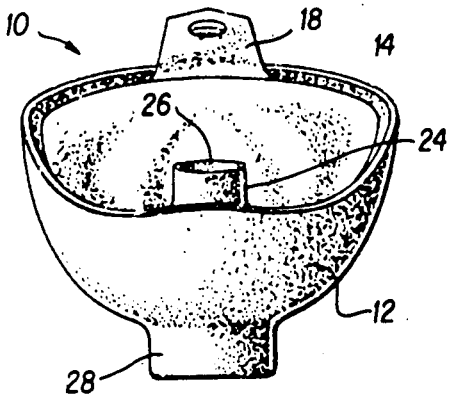
FIG. 5 is a front elevational view of the device of FIG. 1.
Figure 6:
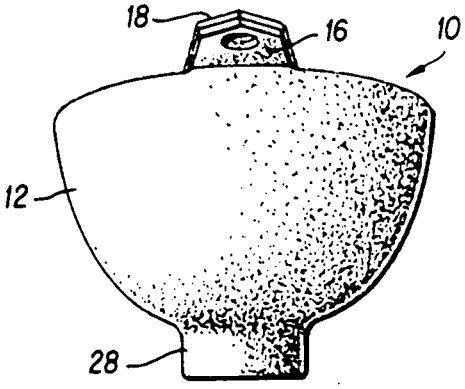
FIG. 6 is a rear elevational view of the device of FIG. 1.
Figure 3:
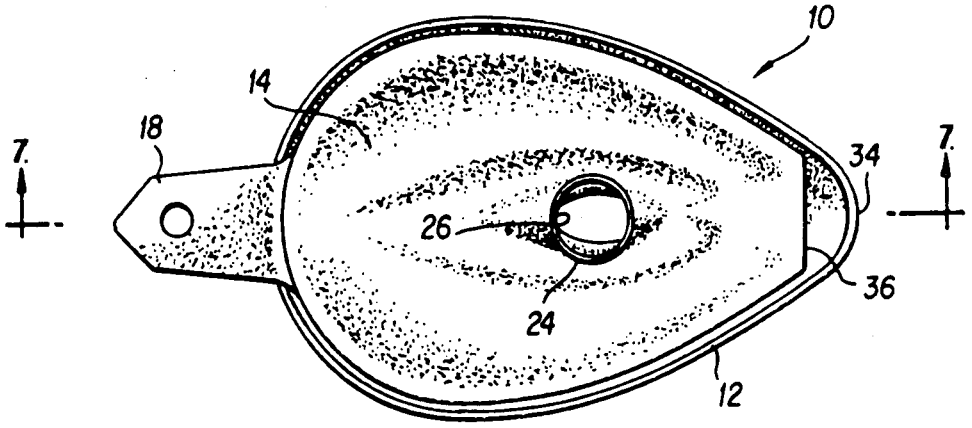
FIG. 3 is a top plan view of the device of FIG. 1.
Figure 4:
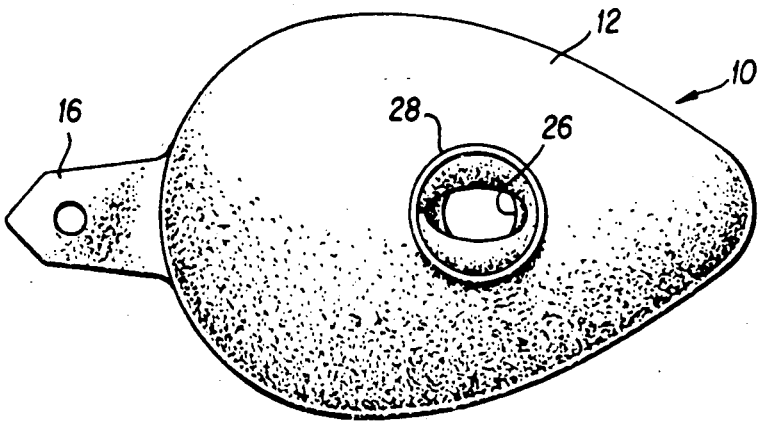
FIG. 4 is a bottom plan view of the device of FIG. 1.

The bowl-shaped member 12 has a substantially teardrop shape in plan view as can be seen best in FIGS. 1, 3 and 4. This substantially teardrop configuration terminates in a substantially pointed frontal portion 34 which is spaced from a foreshortened end 36 of cover member 14, thereby providing an opening through which an overflow from the urine specimen introductory collector 10 may be had. The rearward portion 38 of the bowl-shaped member 12 is substantially higher than the frontal portion 34 as can readily be seen in FIGS. 2 and 7. With the aid of handle portions 16, 18, the user, most customarily of the female gender, can hold the urine specimen introductory collector 10 and attached collection container 32 in close proximity to her body with the handle portion being uppermost and the frontal portion 34 of the bowl-shaped member 12 at the bottom, in order to urinate through opening 26 of the raised cylindrical boss 24, directly into the collection container 32. The substantial in-line registry of the opening 26 with the opening in collection container 32 is best seen in FIGS. 3, 4 and 7. With the urine specimen introductory collector 10 and attached collection container 32 held in its operative position with the handle portions 16 and 18 at the top, the opening between the foreshortened end 36 of cover 14 with the pointed forward portion of the bowl-shaped member 12, permits overflow urine to pass into a conventional toilet. Because the sides of bowl-shaped member 12 taper inwardly as can be seen in FIGS. 1, 5 and 6, the sides are engaged by the marginal edges of cover member 14 to limit the depth to which the cover member 14 can penetrate the bowl-shaped member 12 as is illustrated in FIG. 1. When the rear prtion 38 of the bowl-shaped member 12 is rotated 90° clockwise from its FIG. 7 position to its position of use, the pivotally mounted cover member 14 pivots away from the bottom of the bowl-shaped member 12 under the influence of gravity, thus aiding in the ability of the device to handle overflow urine should that occur. The material used for the urine specimen introductory collector 10 is preferably plastic materials such as styrofoam or polypropylene.

Figure 8:
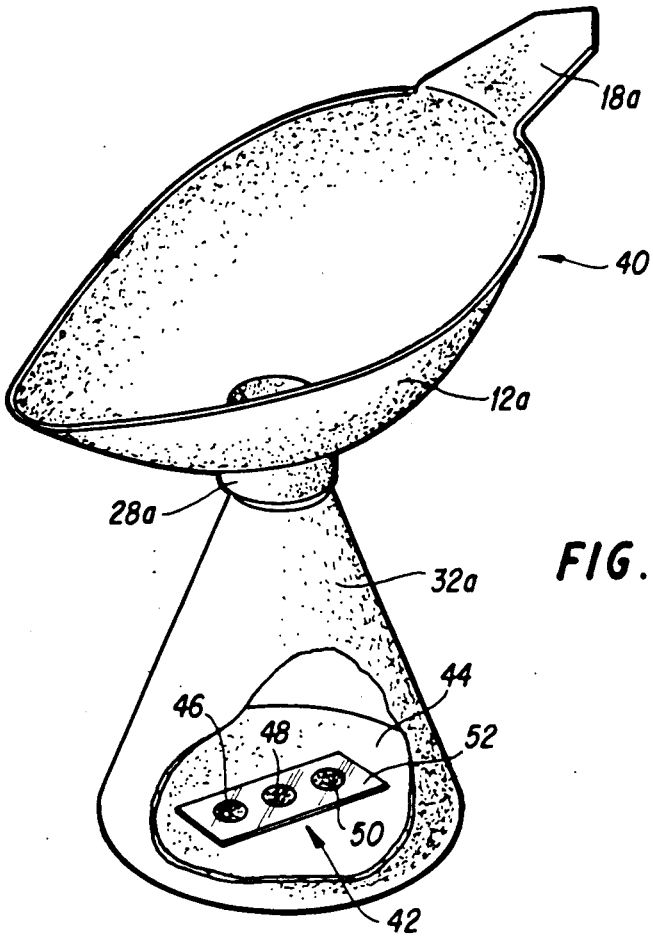
FIG. 8 is a perspective view of a modified introductory collector secured to a collection container with portions broken away to illustrate a temperature sensing member.
Figure 9:
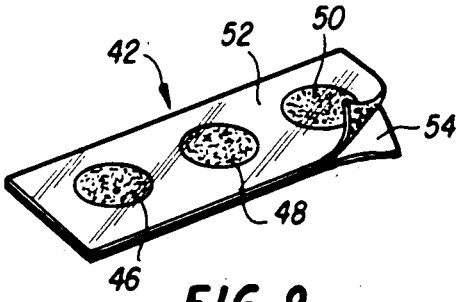
FIG. 9 is a perspective view, drawn to an enlarged scale, of the temperature sensing member of FIG. 8.

Referring now to FIG. 8 of the drawings, there is illustrated a modified urine specimen collector, indicated generaly at 40, which is devoid of a splash guard protector. However, urine specimen collector 40 has a bowl-shaped portion 12a, integral handle 18a and a tubular outlet stem 28a. Collector 40 is illustrated to be threadedly connected to collection container 32a.

An irreversible temperature sensitive member, indicated generally by numeral 42, is adhesively secured to the inside bottom 44 of collection container 32a. The temperature sensitive member 42 has temperature sensitive disks 46, 48, 50 mounted on a suitable backing member 52. A pressure sensitive adhesive is provided on the underside of backing member 52 protected by a peel off adhesive cover member 54. In practice, the adhesive cover member 54 is removed from the pressure sensitive adhesive on backing member 52 and applied to the inside bottom 44 of collection container 32a with the aid of tweezers or any other suitable instrument.

Disks 46, 48 and 50 are each preset in their manufacture to change color at a predetermined temperature. While some tolerances in the preset temperature can be tolerated, it is essential that at least one disk be preset on each side of the normal body temperature of 98.6° F. For example, disk 46 may be preset to change color at about 90° F., disk 48 may be preset to change color to about 95° F. and disk 50 may be preset to change color at about 100° F. With this arrangement, disks 46 and 48 would change color when a normal urine specimen is tested.

Figure 10:
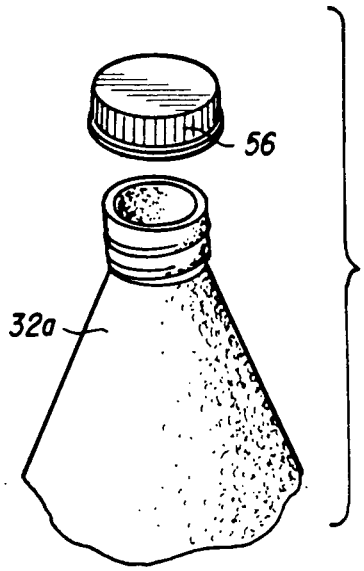
FIG. 10 is a fragmentary, exploded view of a collection container and cap therefor.

FIG. 10 illustrates that the collection container 32a is initially provided with a tamperproof closure member 56. The invention will perform satisfactorily with any tamperproof closure member and this forms no part of the present invention.

Figure 11:
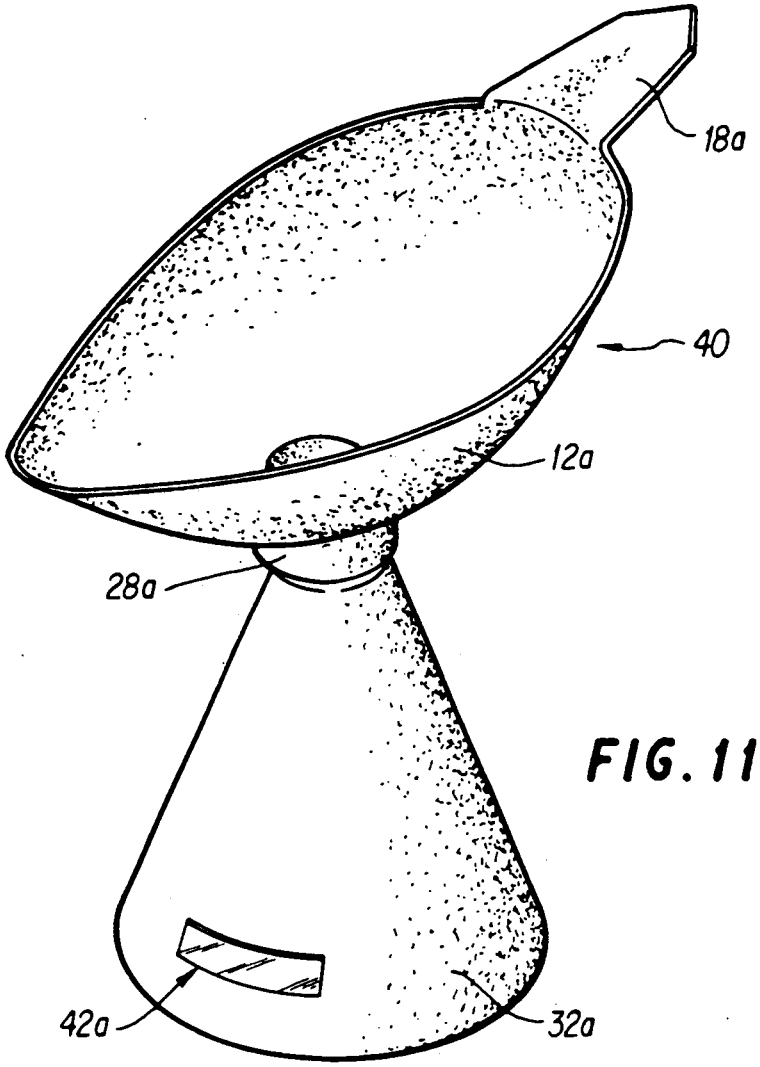
FIG. 11 is a perspective view of the introductory collector and collection container of FIG. 8 with an alternative positioning for and modified form of a temperature sensing member.
Figure 12:
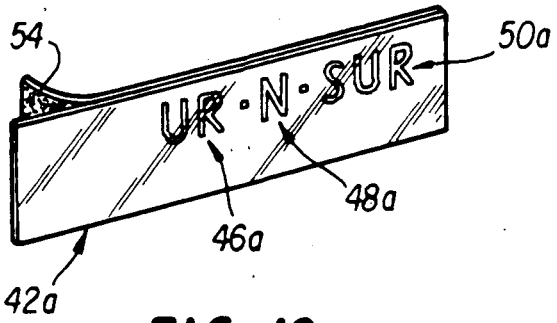
FIG. 12 is a perspective view of the modified form of temperature sensing member shown in FIG. 11.

Referring now to FIGS. 11 and 12, a modified form and placement are shown for the temperature sensitive member, designated generally at 42a in these figures. The specimen collector 40 with its bowl-shaped portion 12a and integral handle 18a are the same as shown in FIG. 8. Similarly, the tubular outlet stem 28a leading to collection container 32a are the same as in FIG. 8.

The temperature sensitive member 42a is attached to the exterior of collection container 32a after a peel off adhesive cover member 54 has been removed. The temperature sensitive member 42a is then adhesively secured to the exterior of collection container 32a at a height below the level of urine that has already been deposited in collection container by the person whose urine is to be tested. In this manner a sufficiently close heat transfer is established by heat conduction through collection container 32a.

In place of discs 46, 48 and 50, the temperature sensitive member 42a has a letter or groups of letters and symbols 46a, 48a and 50a. For example, the letters UR may be preset to change color at about 90° F., the letter and symbol -N may be preset to change color at about 95° F.; and the symbol and letters -SUR may be preset to change color at 100° F. with the letters and symbols corresponding to 46a, 48a and 50a respectively. Once again the temperature sensitive member 42a is preferably irreversible so that a spurious urine sample may easily be detected. In this embodiment, the temperature of the urine is obtained by heat conduction through the collection container 32a. A sufficiently close heat transfer would not be established if the temperature sensitive member were attached to collector container 32a above the level of urine specimen within the collector container.

While invention has been illustrated and described with respect to preferred embodiments thereof, it will be recognized that the invention may be otherwise variously embodied and practiced within the scope of the claims which follow.

I claim:

1. In a urine specimen collector for detecting spurious, fraudulent, non-authentic or non-current urine specimens, the combination which comprises:

a. a bowl-shaped member generally oval in crosssection having a relatively shallow portion at one end and a steeper portion at an opposite end, i. handle means connected to said bowl-shaped member at said steeper portion, ii. said bowl-shaped member having a bottom opening to permit drainage to a collection container, b. a cover member providing a splash guard for said bowl-shaped member when urine is being deposited in said bowl-shaped member, i. said cover member being secured to said handle means, ii. said cover member being pivotally movable under the influence of gravity away from said bowl-shaped member when said bowl-shaped member is held vertically beneath said handle means in which position any excess urine flows out of said shallow portion into a toilet, urinal or other vessel for disposing of said excess urine, c. and a temperature sensitive member secured externally of said collection container.

2. In a urine specimen collector as defined in claim 1 wherein said temperature sensitive member includes at least one portion which will indicate a temperature for the specimen that is slightly less than normal body temperature and at least one other portion which will indicate a temperature for the specimen that is slightly in excess of the normal body temperature.

3. In a urine specimen collector for detecting spurious, fraudulent, non-authentic or non-current urine specimens, the combination which comprises:

a. a funnel-shaped member having a bowl portion generally oval in cross-section and a bottom drainage port for directing a urine specimen into a collection container, i. said funnel-shaped member having an open top, a relatively shallow portions at one end and a steeper portion at an opposite end, ii. a handle secured to said steeper portion whereby said funnel-shaped member may be held by said handle in an uppermost position permitting any excess urine to flow out of said shallow portion into a toilet, urinal or other vessel for disposing of said excess urine, b. a urine specimen collection container secured to said bottom drainage port, c. and a temperature sensitive member secured externally of said urine specimen collection container at a height below the level of a urine specimen within said collection container with said temperature sensitive member being capable of signalling a spurious urine specimen by heat conduction through said urine specimen collection container.

4. The combination as defined in claim 3 wherein said temperature sensitive member contains portions which change color irreversibly at preselected temperatures.

5. A method of detecting a spurious, fraudulent, non-authentic or non-current urine specimen which comprises:

a. attaching a temperature sensitive member to the exterior of a urine specimen receptacle below the height of urine specimen to be deposited within said receptacle, b. securing to said urine specimen receptacle a funnel-shaped member having a bowl portion and a bottom drainage port for directing a urine specimen into said urine specimen receptacle, c. and presenting said urine specimen receptacle to the person whose urine is to be tested, said temperature sensitive member including at least one portion which will will indicate a temperature for the specimen slightly less than normal body temperature and at least one other portion which will indicate a temperature for the specimen slightly in excess of normal body temperature.

*6. In a single use urine specimen collector container for detecting spurious, fraudulent, non-authentic or non-current urine specimens, the combination which comprises:*

*a. a urine specimen collection container,*

*b. and a temperature sensitive member which includes at least one portion which will indicate a temperature for the specimen that is slightly less than normal body temperature and at least one portion which will indicate a temperature for the specimen that is slightly in excess of the normal body temperature secured externally of said urine specimen collection container at a height below the level of a urine specimen to be deposited within said collection container with said temperature sensitive member being capable of signalling a spurious urine specimen by heat conduction through said urine specimen collection container.*

*7. A method of detecting a spurious, fraudulent, non-authentic or non-current urine specimen which comprises:*

*presenting a urine specimen collection container to the person whose urine is to be tested;*

*collecting a urine sample; and*

*determining whether said urine sample is spurious, fraudulent, non-authentic or non-current by reading a temperature sensitive member secured in thermal relationship to the exterior of said container at a height below the level of the urine sample which temperature member will indicate at one portion a temperature that is slightly less than normal body temperature and at another portion a temperature that is slightly in excess of the normal body temperature.*

* * * * *